United States Patent
Badano et al.

[11] Patent Number: 6,106,793
[45] Date of Patent: Aug. 22, 2000

[54] PROCESS FOR THE AMMONIA AND METHANOL CO-PRODUCTION

[75] Inventors: Marco Badano, Lugano-Besso, Switzerland; Franco Fabbri, Milan, Italy; Ermanno Filippi, Castagnola, Switzerland

[73] Assignee: Methanol Casale S.A., Lugano-Besso, Switzerland

[21] Appl. No.: 08/983,496

[22] PCT Filed: Nov. 19, 1996

[86] PCT No.: PCT/IB96/01248

§ 371 Date: Dec. 29, 1997

§ 102(e) Date: Dec. 29, 1997

[87] PCT Pub. No.: WO97/19018

PCT Pub. Date: May 29, 1997

[30] Foreign Application Priority Data

Nov. 23, 1995 [CH] Switzerland .............................. 3309/95

[51] Int. Cl.$^7$ ................................ C01C 1/00; C01C 1/04
[52] U.S. Cl. ........................... 423/359; 422/148; 422/189
[58] Field of Search ............................ 423/359; 422/129, 422/148, 189, 198

[56] References Cited

U.S. PATENT DOCUMENTS

| | | |
|---|---|---|
| 3,598,527 | 8/1971 | Quartulli et al. . |
| 4,315,900 | 2/1982 | Nozawa et al. . |
| 4,367,206 | 1/1983 | Pinto ........................................ 423/359 |
| 4,411,877 | 10/1983 | Notman ................................... 423/359 |
| 4,681,745 | 7/1987 | Pinto ........................................ 423/359 |
| 5,167,933 | 12/1992 | Norsk ...................................... 423/359 |
| 5,180,570 | 1/1993 | Lee et al. ................................ 423/359 |

FOREIGN PATENT DOCUMENTS

| | | |
|---|---|---|
| 0342610 | 11/1989 | European Pat. Off. . |
| 1472437 | 4/1989 | U.S.S.R. . |
| 2252317 | 8/1992 | United Kingdom . |

*Primary Examiner*—Wayne Langel
*Attorney, Agent, or Firm*—Sughrue, Mion, Zinn, Macpeak & Seas, PLLC

[57] ABSTRACT

A process for ammonia and methanol co-production in a plant comprising a first primary reforming section (11) and a secondary reforming section (12) arranged in series, an ammonia synthesis section (13) and a methanol synthesis section (22), is distinguished by the fact that ammonia and methanol are produced in independent synthesis processes where the heat required for the reforming reaction in the methanol process is advantageously obtained by utilizing the high heat content present in the gas flow coming from the secondary reforming section (12) of the ammonia process.

17 Claims, 1 Drawing Sheet

PROCESS FOR THE AMMONIA AND METHANOL CO-PRODUCTION

FIELD OF APPLICATION

The present invention relates to a process for the ammonia and methanol co-production in a plant comprising a first primary reforming section and a secondary reforming section arranged in series, an ammonia synthesis section and a methanol synthesis section, said process comprising the steps of:

feeding methane and steam to the first primary reforming section;

reacting the methane and steam in the first primary reforming section and successively in the secondary reforming section to obtain a first gaseous phase comprising CO, $CO_2$ and $H_2$.

In the description given below and in the following claims, the term: "in-situ" modernization, is understood to mean the on-site modification of a pre-existing reactor in order to improve its performance and obtain e.g. greater production capacity and/or greater conversion yield and/or reduction in energy consumption.

In the description given below and in the following claims, the term: 'synthesis section', is understood to mean generally all of that part of the plant concerned with ammonia or methanol production and operationally located downstream of the reforming sections.

In the description given below and the following claims, the term: 'methane', is understood to mean generally a raw material source of hydrogen and carbon, such as e.g. methane itself or a mixture of liquid and/or gaseous hydrocarbons such as natural gas and naphtha.

The present invention also relates to a plant for ammonia and methanol co-production for carrying out the above mentioned process, as well as to a modernization method for an ammonia synthesis plant and to a modernization method for an ammonia and methanol co-production plant.

As known, there is an ever growing requirement in the field of ammonia and methanol co-production to provide synthesis processes easy to implement, which allow achievement of ever higher production capacities at low operating and investment costs and at low energy consumption.

PRIOR ART

For the purpose of meeting the above mentioned requirement, there have recently been proposed in the field synthesis processes for ammonia and methanol co-production, wherein a flow of gas rich in CO, $CO_2$ and $H_2$ coming from the secondary reforming section of an ammonia synthesis plant, is diverted to a synthesis section for methanol production. The unreacted gas is subsequently reintroduced into the synthesis section of the ammonia plant.

Although advantageous in some ways, the above described processes exhibit a series of drawbacks, the first of which is that the production capacity of ammonia and that of methanol are strictly correlated and depend mainly on the methane and steam load which can be fed to the reforming sections.

In other words, as the total production capacity of the co-production plant operating in accordance with these processes is substantially determined by the loading capacity of the reforming sections, in a full-capacity operating situation an increase in the production of methanol causes inevitably an approximately equivalent reduction in the ammonia production, and vice versa.

This means that if it is desired to obtain high production capacity of both ammonia and methanol it is necessary, according to the prior art processes, to size the reforming sections correspondingly so that they are capable of supporting a load of reagents permitting achievement of the desired production capacity. In addition, the ammonia and methanol synthesis sections must also be oversized to meet any load increases caused by changes in methanol and ammonia production.

Consequently, if high production capacity of both ammonia and methanol is required, the co-production plant which must be provided for implementation of the above mentioned processes exhibits considerable structural complexity, high investment and operating costs, and high energy consumption.

Because of these disadvantages, the prior art ammonia and methanol co-production processes have heretofore found slight application despite the growing demand in the industry.

SUMMARY OF THE INVENTION

The problem underlying the present invention is to provide a process for ammonia and methanol co-production which would be simple to carry out and permit achieving of high production capacity of both ammonia and methanol with low investment and operation costs and low energy consumption.

This problem is solved according to the present invention by a process for ammonia and methanol co-production of the above mentioned type, which is characterized in that it comprises the steps of:

feeding methane and steam to a reaction zone defined in a second primary reforming section of the 'exchanger' type;

feeding the first gaseous phase externally to the reaction zone in the second primary reforming section;

reacting the methane and steam in the reaction zone by indirect heat exchange with the first gaseous phase to obtain a second gaseous phase comprising CO, $CO_2$ and $H_2$;

feeding the first gaseous phase coming from the second primary reforming section to the ammonia synthesis section;

feeding the second gaseous phase coming from the second primary reforming section to the methanol synthesis section.

In the description given below and in the following claims, the term: 'primary reforming section of the 'exchanger' type' is understood to mean a primary reforming section for the production of CO, $CO_2$ and $H_2$, in which the reaction heat instead of being supplied by combustion of a fuel (e.g. natural gas or naphtha), it is supplied by indirect heat exchange with a hot gas flow fed to this section. In this specific case the hot gas flow is represented by the first gaseous phase coming from the secondary reforming section.

Reformers of the 'exchanger' type are generally known in the state of the art and are usually employed in ammonia synthesis processes in replacement of the primary reformer.

These reformers define within them a reaction zone through which the gaseous reagents pass. The reforming reaction is made possible by the heat transmitted by a hot gas flowing externally to the reaction zone.

Reformers of this type consist for example of a plurality of pipes filled with catalyst, outside of which (shell side) is made to flow a hot gas which yields reaction heat by indirect heat exchange to a colder gas which flows in the pipes (tube side) reacting.

The reformer of the 'exchanger' type can also be provided by means of a plurality of contiguous chambers alternately filled with catalyst, wherein hot gas and cold gas are made to flow in the empty chambers and in the filled chambers, respectively. In this case, the chambers are made e.g. in mutually parallel walls or concentric cylinders.

Advantageously, thanks to the process according to the present invention it is possible to achieve an independent production of ammonia and methanol, which allows to obtain high production capacities in a simple way, with low investment and operating costs and with low energy consumption.

Indeed, according to the present invention, the high heat content in the first gaseous phase coming from the secondary reforming section, is advantageously utilized as reaction heat to produce in a second primary reforming section a second gaseous phase comprising CO, $CO_2$ and $H_2$ for the methanol synthesis process.

In this manner, the synthesis gas production for ammonia and methanol no longer takes place in common reforming sections, with all the disadvantages thereof with reference to the prior art co-production processes. The process according to the present invention calls for production of methanol synthesis gas in a second, independent, primary reforming section.

Advantageously, this second primary reforming section is fed with methane and steam which react by indirect heat exchange with a gaseous phase coming from the secondary reforming section of the ammonia process, with recovery of the heat contained in the gaseous phase while avoiding the use of energy sources external to the co-production process such as the fuels generally employed in reforming sections.

Preferably, the temperature of the first gaseous phase coming from the secondary reforming section and fed to the second primary reforming section is between 900° C. and 1100° C., so as to supply heat ensuring nearly complete conversion of the methane and steam fed to the second primary reforming section.

Preferably the process according to the present invention comprises the additional steps of:

taking at least part of said second gaseous phase coming from said second primary reforming section;

feeding this at least part of the second gaseous phase to the first primary reforming section.

Thanks to this particular embodiment of the present invention, it is possible to control the quantity of gas to be sent to the methanol synthesis section according to the quantity of methanol it is desired to produce. In addition, in this manner it is also possible to meet a situation in which methanol production is temporarily not required for reasons of market demand or for maintenance of the synthesis section.

The excess gas produced in the second primary reforming section and comprising CO, $CO_2$ and $H_2$ not sent to the methanol synthesis section is advantageously recycled to the first primary reforming section to reduce the methane and steam load to be fed to the first primary reforming section and consequently also heat consumption of this section.

Advantageously the co-production process according to the present invention also comprises the additional steps of:

taking a purge gaseous flow comprising CO, $CO_2$ and $H_2$ coming from the methanol synthesis section;

feeding this purge gaseous flow to the first primary reforming section.

In this manner, the purge gas coming from the methanol synthesis section and rich in CO, $CO_2$ and $H_2$ can be advantageously recovered and recycled to the first primary reforming section to achieve also in this case a reduction of the methane and steam load to be fed to the first primary reforming section and consequently of the heat consumption of this section and of the total energy consumption of the co-production plant.

To implement the above mentioned process the present invention advantageously makes available a plant for ammonia and methanol co-production comprising:

a first primary reforming section and a secondary reforming section arranged in series to obtain a first gaseous phase comprising CO, $CO_2$ and $H_2$;

means of feeding methane and steam to the first primary reforming section;

an ammonia synthesis section;

a methanol synthesis section;

characterized in that it comprises:

a second primary reforming section of the 'exchanger' type to obtain a second gaseous phase comprising CO, $CO_2$ and $H_2$;

means of feeding methane and steam to a reaction zone defined in the second primary reforming section;

connection means between the secondary reforming section and the second primary reforming section for feeding the first gaseous phase externally to the reaction zone;

means for indirect heat exchange between the first gaseous phase and the methane and steam in the second primary reforming section;

connection means between the second primary reforming section and the methanol synthesis section for feeding to the latter a second gaseous phase comprising CO, $CO_2$ and $H_2$;

connection means between the second primary reforming section and the ammonia synthesis section for feeding to the latter said first gaseous phase.

In accordance with another aspect of the present invention there is also made available a method of modernizing an ammonia synthesis plant of the type comprising a first primary reforming section and a secondary reforming section arranged in series to obtain a first gaseous phase comprising CO, $CO_2$ and $H_2$, means for feeding methane and steam to the first primary reforming section, an ammonia synthesis section, said method comprising the steps of:

providing a methanol synthesis section;

providing a second primary reforming section of the 'exchanger' type;

providing means for feeding methane and steam to a reaction zone defined in the second primary reforming section;

providing connection means between the secondary reforming section and the second primary reforming section for feeding the first gaseous phase externally to the reaction zone;

providing means for indirect heat exchange between the first gaseous phase and the methane and steam in the second primary reforming section;

providing connection means between the second primary reforming section and the methanol synthesis section for feeding to the latter a second gaseous phase comprising CO, $CO_2$ and $H_2$;

providing connection means between the second primary reforming section and the ammonia synthesis section for feeding to the latter said first gaseous phase.

In accordance with another aspect of the present invention, there is also made available a method of modernizing an ammonia and methanol co-production plant of the type comprising a first primary reforming section and a secondary reforming section arranged in series to obtain a first gaseous phase comprising CO, $CO_2$ and $H_2$, means for feeding methane and steam to the first primary reforming section, an ammonia synthesis section, a methanol synthesis section, said method comprising the steps of:

- providing a second primary reforming section of the 'exchanger' type;
- providing means for feeding methane and steam to a reaction zone defined in the second primary reforming section;
- providing connection means between the secondary reforming section and the second primary reforming section for feeding the first gaseous phase externally to the reaction zone;
- providing means of indirect heat exchange between the first gaseous phase and the methane and steam in the second primary reforming section;
- providing connection means between the second primary reforming section and the methanol synthesis section for feeding to the latter a second gaseous phase comprising Co, $CO_2$ and $H_2$;
- providing connection means between the second primary reforming section and the ammonia synthesis section for feeding to the latter said first gaseous phase.

Thanks to the above mentioned modernization methods for an existing plant it is possible to obtain an ammonia and methanol co-production process simple to carry out, capable of achieving high production capacities of both ammonia and methanol at low operating and investment costs and with low energy consumption.

The characteristics and advantages of the present invention are set forth in the description of an embodiment thereof given below by way of non-limiting example with reference to the annexed FIGURE.

DETAILED DESCRIPTION OF A PREFERRED EMBODIMENT

Figure 1:
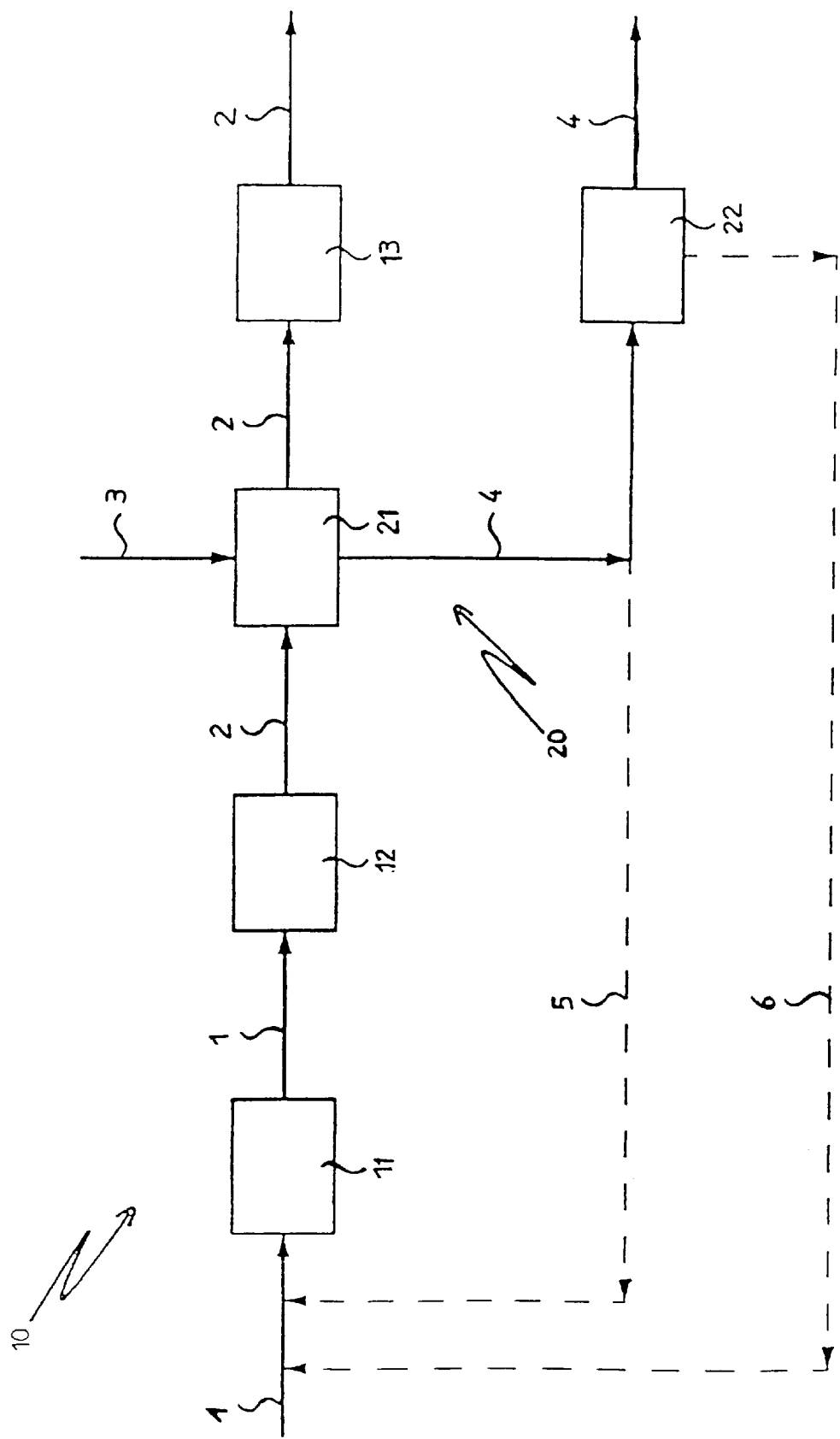
FIG. 1 shows a block diagram of the ammonia and methanol co-production process according to the present invention.

FIG. 1 shows a block diagram illustrating the steps of the ammonia and methanol co-production process in accordance with the present invention.

This process permits simultaneous achievement of high production capacity of ammonia (e.g. between 1000 and 2500 metric tons per day) and methanol (e.g. between 700 and 1700 metric tons per day).

Reference number 10 indicates generally a portion of the block diagram illustrating the steps of the ammonia production process.

In this portion 10, blocks 11, 12 and 13 indicate respectively a first primary reforming section, a secondary reforming section and an ammonia synthesis section. The latter includes in addition to the actual synthesis section, the high- and low-temperature CO conversion sections, the $CO_2$ separation section and the methanation section. The above mentioned primary and secondary reforming sections are catalytic.

Reference number 20 indicates generally a portion of the block diagram illustrating the steps of the methanol production process.

In this portion 20, blocks 21 and 22 indicate respectively a second primary reforming section and a methanol synthesis section. The latter also includes in addition to the actual synthesis section, the $H_2O$ condensation and separation section and the methanol purification section.

Advantageously, the second primary reforming section indicated by the block 21 is of the 'exchanger' type, and preferably of the type equipped with a plurality of pipes filled with catalyst in which the reforming reaction takes place.

To the first primary reforming section indicated by the block 11 is fed flow line 1, which represents a first gaseous flow comprising methane and steam. The temperature of this first gaseous flow is the conventional temperature for an ammonia plant, e.g. 300–650° C.

Passing through the first primary reforming section and the secondary reforming section (blocks 11 and 12), the methane and steam contained in the first gaseous flow react to obtain a first gaseous phase comprising CO, $CO_2$ and $H_2$.

The flow line 2 represents this first gaseous phase coming from the secondary reforming section indicated by the block 12. The temperature of the gas flow 2 is preferably between 980° C. and 1050° C.

Advantageously, the flow line 2 traverses on the shell side the second primary reforming section represented by the block 21 where it cools down by indirect heat exchange with a gaseous flow comprising methane and steam fed tube side to the block 21, and indicated by the flow line 3.

Upon outlet from the second primary reforming section (block 21), the gas flow 2 is fed to the ammonia synthesis section (block 13) at a temperature between 30° C. and 600° C.

Upon outlet from block 13 the flow 2 contains mainly ammonia.

The gas flow represented by the flow line 3 is fed to the second primary reforming section (block 21) at a temperature between 200° C. and 600° C. Here the gas flow 3 reacts advantageously by indirect heat exchange with the gas flow indicated by the flow line 2, to obtain a second gaseous phase comprising CO, $CO_2$ and $H_2$.

The flow line 4 indicates this second gaseous phase coming from the second primary reforming section (block 21). The temperature of the gas flow 4 is generally between 700° C. and 1000° C.

The gas flow 4 is fed into the methanol synthesis section represented by block 22. Upon outlet from the block 22 the flow 4 contains mainly methanol.

The operating conditions of the synthesis sections for the production of ammonia or methanol (blocks 13 and 22 respectively), as well as the types of reaction taking place in them, are the conventional ones of an ammonia and methanol plant respectively, known to those skilled in the art and therefore not described in greater detail.

The pressure of the gas flows 1 to 4 is preferably between 1 bar and 60 bar.

In accordance with the co-production process according to the present invention a first flow of methane and steam is fed to a first primary reforming section (block 11) and is reacted in this reforming section and subsequently in a secondary reforming section (blocks 11 and 12) to obtain a first gaseous phase comprising CO, $CO_2$ and $H_2$.

Advantageously, in accordance with further steps of the present invention, a flow of methane and steam is fed to a reaction zone defined in a second primary reforming section (block 21). At the same time, the first gaseous phase is fed externally to the reaction zone of the second primary reforming section. Within this reaction zone, methane and steam are reacted by indirect heat exchange with the first gaseous phase to obtain a second gaseous phase comprising CO, $CO_2$ and $H_2$. The first gaseous phase coming from the second primary reforming section is then fed to an ammonia synthesis section (block 13), while the second gaseous phase is fed to a methanol synthesis section (block 22).

In this manner, ammonia and methanol are produced in independent synthesis processes, where the heat required for the methane reforming reaction in the methanol process is advantageously obtained by utilizing the high heat content in the gas flow coming from the secondary reforming section of the ammonia process.

In accordance with another particularly advantageous embodiment of the present invention, but not shown, the co-production process comprises the additional step of cooling the second gaseous phase (flow line 4) coming from the second primary reforming section (block 21) by indirect heat exchange with cooling water, to obtain high pressure and temperature steam e.g. between 5 bar and 130 bar and between 150° C. and 550° C. respectively.

So doing, the heat of the gaseous phase coming from the second primary reforming section is advantageously recovered for production of steam with a high heat level, which can be used depending on requirements e.g. in the other sections of the ammonia and methanol co-production plant.

The temperature of the gas flow 4 which underwent the above mentioned cooling step is preferably between 30° C. and 300° C.

The heat in the gas flow 4 coming from the block 21 can alternatively be recovered to preheat by indirect heat exchange the methane or the gaseous flow comprising methane and steam to be fed to the second primary reforming section.

In accordance with an alternative embodiment of the process according to the present invention, part of the second gaseous phase (flow line 4) coming from block 21 can be advantageously diverted to the first primary reforming section (block 11) of the ammonia process. This permits adapting the methanol process production capacity depending on the desired quantity of methanol and at the same time to reduce the methane load to be fed to the ammonia process with resulting saving of raw materials and energy.

In FIG. 1, this embodiment is shown in broken lines by flow line 5.

In case only ammonia production is requested, then all the second gaseous phase coming from block 21 is advantageously sent (flow line 5) to the first primary reforming section (block 11) of the ammonia process, as shown in FIG. 1, or directly to the secondary reforming section (block 12).

In another alternative and particularly advantageous embodiment of the process according to the present invention, a purge gaseous flow comprising CO, $CO_2$ and $H_2$ coming from the methanol synthesis section (block 22) is sent to the first primary reforming section (block 11) of the ammonia process to obtain a further lightening of the methane load to be fed to this reforming section.

The pressure and the temperature of the purge gaseous flow fed to the first primary reforming section are generally between 1 bar and 60 bar and between 30° C. and 600° C. respectively.

In FIG. 1, this embodiment is shown in broken lines by flow line 6.

The ammonia and methanol co-production plant according to the present invention includes the sections represented by the blocks 11–13 and 21–22 of FIG. 1.

At the inlet and between the sections making up the above mentioned plant are provided suitable feeding and connection means respectively of types known in the industry, e.g. ducts, piping and the like represented schematically by the flow lines 1–6 of FIG. 1.

Inside the second primary reforming section represented by the block 21 are also provided suitable means for indirect heat exchange between the gas flows 2 and 3. These means can comprise one or more heat exchangers.

Advantageously, the plant according to the present invention also provides a cooling section (not shown) for cooling the gas flow 4 coming from block 21 by indirect heat exchange with cooling water. A cooling section of this type can comprise e.g. a boiler for steam production.

In order to increase the methanol production, a gas flow comprising $CO_2$ (not shown) is advantageously added to flow line 3 or 4, preferably to flow line 4.

In fact, since the gas flowing through line 4 is generally very rich in $H_2$, the above addition allows an improvement in the stoichiometric ratio $CO_2/H_2$ which results in an improvement of the methanol synthesis conditions.

In accordance with the present invention, the method of modernizing an existing ammonia and methanol co-production plant comprising a first primary reforming section and a secondary reforming section (blocks 11 and 12) arranged in mutual series, an ammonia synthesis section (block 13) and a methanol synthesis section (block 22), advantageously provides the steps of providing a second primary reforming section (block 21) of the 'exchanger' type comprising means suitable for indirect heat exchange, and of providing appropriate means for feeding to the second primary reforming section (block 21) and connection between the secondary reforming section and the second primary reforming section (blocks 12 and 21) as between the second primary reforming section and the ammonia and methanol synthesis sections (blocks 21, 13, 22).

The method for modernization of an existing ammonia synthesis plant according to the present invention provides the additional step of providing, in addition to the second primary reforming section, also a methanol synthesis section (block 22).

Advantageously, in an alternative embodiment of the above modernization methods, not shown, a cooling section for cooling the gas flow 4 by indirect heat exchange with cooling water for the production of steam at high heat level, is provided between blocks 21 and 22.

In addition, according to another embodiment of the modernization methods in accordance with the present invention, suitable connection means between the second and first primary reforming sections (blocks 21 and 11) and between the methanol synthesis section and the first primary reforming section (block 11) are advantageously provided. In this manner it is possible to recover excess CO, $CO_2$ and $H_2$ from the methanol synthesis process and send it to the ammonia synthesis process to lighten the methane load to be sent to the reforming sections of the ammonia plant and thus achieve a reduction in energy and raw material consumption.

In the special situation in which only ammonia is intended to be produced, then the above modernization methods advantageously allow an increase in the production of the reforming sections with respect to an pre-existing ammonia synthesis plant, thanks to the provision of the second primary reforming section.

From the foregoing, the numerous advantages achieved by the present invention are clear. In particular there is provided an ammonia and methanol co-production process simple to implement, capable of achieving high production capacities both for ammonia and methanol with low operating and investment costs and low energy consumption. Moreover, in the case of modernization of an ammonia synthesis plant or an ammonia and methanol co-production plant it is possible to achieve high production capacity of methanol while holding unchanged the ammonia production capacity.

What is claimed is:

1. Process for the ammonia and methanol co-production in a plant comprising a first primary reforming section and a secondary reforming section arranged in series, an ammonia synthesis section and a methanol synthesis section, said process comprising the steps of:

feeding methane and steam to said first primary reforming section;

reacting said methane and steam in said first primary reforming section and subsequently in said secondary reforming section to obtain a first gaseous phase comprising CO, $CO_2$ and $H_2$;

the process comprising the steps of:

feeding methane and steam to a reaction zone defined in a second primary reforming section of the 'exchanger' type;

feeding said first gaseous phase externally to said reaction zone in said second primary reforming section;

reacting in said reaction zone said methane and steam by indirect heat exchange with said first gaseous phase to obtain a second gaseous phase comprising CO, $CO_2$ and $H_2$;

feeding said first gaseous phase coming from said second primary reforming section to said ammonia synthesis section; and feeding said second gaseous phase coming from said second primary reforming section to said methanol synthesis section.

2. Process according to claim 1, wherein the temperature of the first gaseous phase fed to the second primary reforming section is between 900° C. and 1100° C.

3. Process according to claim 1, further comprising the additional step of cooling said second gaseous phase coming from said second primary reforming section by indirect heat exchange with cooling water to obtain high pressure and temperature steam.

4. Process according to claim 1, further comprising the additional steps of:

taking at least part of said second gaseous phase coming from said second primary reforming section; and feeding said at least part of said second gaseous phase to said first primary reforming section.

5. Process according to claim 1, further comprising the additional steps of:

taking a purge gaseous flow comprising CO, $CO_2$ and $H_2$ coming from said methanol synthesis section; and feeding said purge gaseous flow to said first primary reforming section.

6. Plant for ammonia and methanol co-production comprising:

a first primary reforming section (11) and secondary reforming section (12) arranged in series to obtain a first gaseous phase comprising CO, $CO_2$ and $H_2$;

means (1) for feeding methane and steam to said first primary reforming section (11);

a methanol synthesis section (13) and an ammonia synthesis section (22) disposed in parallel in the plant for contemporaneous production of ammonia and methanol;

further comprising:

a second primary reforming section (21) of the 'exchanger' type to obtain a second gaseous phase comprising CO, $CO_2$ and $H_2$;

means (3) for feeding methane and steam to a reaction zone defined in said second primary reforming section (21);

connection means (2) between said secondary reforming section (12) and said second primary reforming section (21) for feeding externally to said reaction zone said first gaseous phase;

means for indirect heat exchange between said first gaseous phase and said methane and steam in said second primary reforming section (21);

direct connection means (4) connecting said second primary reforming section (21) to said methanol synthesis section (22) for feeding to the methanol synthesis section a second gaseous phase comprising CO, $CO_2$ and $H_2$ for the production and methanol; and direct connection means (2) connecting said second primary reforming section (21) to said ammonia synthesis section (13) for feeding to the ammonia synthesis section said first gaseous phase for the production of ammonia.

7. Plant according to claim 6, further comprising a section in fluid communication with said methanol synthesis section (22), for cooling said second gaseous phase coming from said second primary reforming section (21) by indirect heat exchange with cooling water.

8. Plant according to claim 6, further comprising connection means (5) between said second primary reforming section (21) and said first primary reforming section (11) for feeding to the first primary reforming section at least part of said second gaseous phase coming from said second primary reforming section (21).

9. Plant according to claim 6, further comprising connection means (6) between said methanol synthesis section (22) and said first primary reforming section (11) for feeding to the first primary reforming section a purge gaseous flow comprising CO, $CO_2$ and H2 coming from said methanol synthesis section (22).

10. Method of modernizing an ammonia synthesis plant comprising a first primary reforming section (11) and a secondary reforming section (12) arranged in series to obtain a first gaseous phase comprising CO, $CO_2$ and $H_2$, means (1) for feeding methane and steam to said first primary reforming section (11), an ammonia synthesis section (13), said method comprising the steps of:

providing a methanol synthesis section (22) in parallel with said ammonia synthesis section;

providing a second primary reforming section of the 'exchanger' type (21);

providing means (3) for feeding methane and steam to a reaction zone defined in said second primary reforming section (21);

providing connection means (2) between said secondary reforming section (12) and said second primary reforming section (21) for feeding externally to said reaction zone said first gaseous phase;

providing means for indirect heat exchange between said first gaseous phase and said methane and steam in said second primary reforming section (21);

providing direct connection means (4) between said second primary reforming section (21) and said methanol synthesis section (22) for directly feeding to the methanol synthesis section a second gaseous phase comprising CO, $CO_2$ and $H_2$ for methanol production;

providing direct connection means (2) between said second primary reforming section (21) and said ammonia synthesis section (13) for directly feeding to the ammonia synthesis section said first gaseous phase for the production of ammonia contemporaneously with the production of methanol.

11. Method according to claim 10, further comprising providing a section for cooling said second gaseous phase coming from said second primary reforming section by indirect heat exchange with cooling water in fluid communication with said methanol synthesis section (22).

12. Method according to claim 10, further comprising providing connection means (5) between said second primary reforming section (21) and said first primary reforming section (11) for feeding to the first primary reforming section at least part of said second gaseous phase.

13. Method according to claim 10, further comprising providing connection means (6) between said methanol synthesis section (22) and said first primary reforming section (11) for feeding to the first primary reforming section a purge gaseous flow comprising CO, $CO_2$ and $H_2$ coming from said methanol synthesis section.

14. Method of modernizing an ammonia synthesis plant comprising a first primary reforming section (11) and a secondary reforming section (12) arranged in series to obtain a first gaseous phase comprising CO, $CO_2$ and $H_2$, means (1) for feeding methane and steam to said first primary reforming section (11), an ammonia synthesis section (13), a methanol synthesis section (22) disposed in parallel with said ammonia synthesis section for coproduction of ammonia and methanol, said method comprising the steps of:

providing a second primary reforming section of the 'exchanger' type (21);

providing means (3) for feeding methane and steam to a reaction zone defined in said second primary reforming section (21);

providing connection means (2) between said secondary reforming section (12) and said second primary reforming section (21) for feeding externally to said reaction zone said first gaseous phase;

providing means for indirect heat exchange between said first gaseous phase and said methane and steam in said second primary reforming section (21);

providing direct connection means (4) for directly connecting said second primary reforming section (21) to said methanol synthesis section (22) for directly feeding to the methanol synthesis section a second gaseous phase comprising CO, $CO_2$ and $H_2$ for production of methanol; and providing direct connection means (2) between said second primary reforming section (21) and said ammonia synthesis section (13) for directly feeding to the ammonia synthesis section said first gaseous phase for the production of ammonia contemporaneously with the production of methanol.

15. Method according to claim 11, further comprising providing a section for cooling said second gaseous phase coming from said second primary reforming section by indirect heat exchange with cooling water in fluid communication with said methanol synthesis section (22).

16. Method according to claim 11, further comprising providing connection means (5) between said second primary reforming section (21) and said first primary reforming section (11) for feeding to the first primary reforming section at least part of said second gaseous phase.

17. Method according to claim 11, further comprising providing connection means (6) between said methanol synthesis section (22) and said first primary reforming section (11) for feeding to the first primary reforming section a purge gaseous flow comprising CO, $CO_2$ and $H_2$ coming from said methanol synthesis section.

* * * * *